United States Patent
Seydnejad et al.

(10) Patent No.: US 6,519,066 B2
(45) Date of Patent: Feb. 11, 2003

(54) SYSTEM LEVEL STIMULATED RAMAN SCATTERING (SRS) COMPENSATION

(76) Inventors: Saeid Seydnejad, #1005 - 190 Lees Ave., Ottawa, Ontario (CA), K1S 5L5; James Harley, #724 - 195 Clearview Ave., Ottawa, Ontario (CA), K1Z 6S1

( * ) Notice: Subject to any disclaimer, the term of this patent is extended or adjusted under 35 U.S.C. 154(b) by 32 days.

(21) Appl. No.: 09/887,445

(22) Filed: Jun. 25, 2001

(65) Prior Publication Data
US 2002/0114555 A1 Aug. 22, 2002

(51) Int. Cl.[7] .............. G02B 6/26; H04B 10/08
(52) U.S. Cl. ............. 359/161; 359/110; 385/122; 385/123
(58) Field of Search ............... 385/122, 123; 359/110, 161

(56) References Cited

U.S. PATENT DOCUMENTS

| | | | | |
|---|---|---|---|---|
| 5,161,044 A | * | 11/1992 | Nazarathy et al. | 359/157 |
| 5,754,577 A | * | 5/1998 | Casper et al. | 372/38 |
| 5,809,049 A | * | 9/1998 | Schaefer et al. | 372/38 |
| 5,887,093 A | | 3/1999 | Hansen et al. | 385/27 |
| 6,426,822 B1 | * | 7/2002 | Winter et al. | 359/187 |
| 6,427,043 B1 | * | 7/2002 | Naito | 385/123 |

* cited by examiner

*Primary Examiner*—Brian Healy
*Assistant Examiner*—Kevin S Wood

(57) ABSTRACT

The present invention relates to a method and apparatus for system level Stimulated Raman Scattering (SRS) error compensation in an optical fiber network, the network characterized in that it comprises the infrastructure required to measure the power levels of all optical channels using a pilot tone monitoring technique, the compensation method comprises the steps of collecting preceding fiber span system configuration data such as, but not necessarily limited to, the power level of each wavelength and wavelength distribution, SRS error up to that point, fiber type and insertion loss, transmitting the configuration data to a network component having computer readable-code adapted to receive the configuration data, calculating local SRS error values incorporating the transmitted configuration data and leveraging the calculated local SRS error values to correct power levels based on the reported SRS error of the previous spans and the local SRS error.

3 Claims, 6 Drawing Sheets

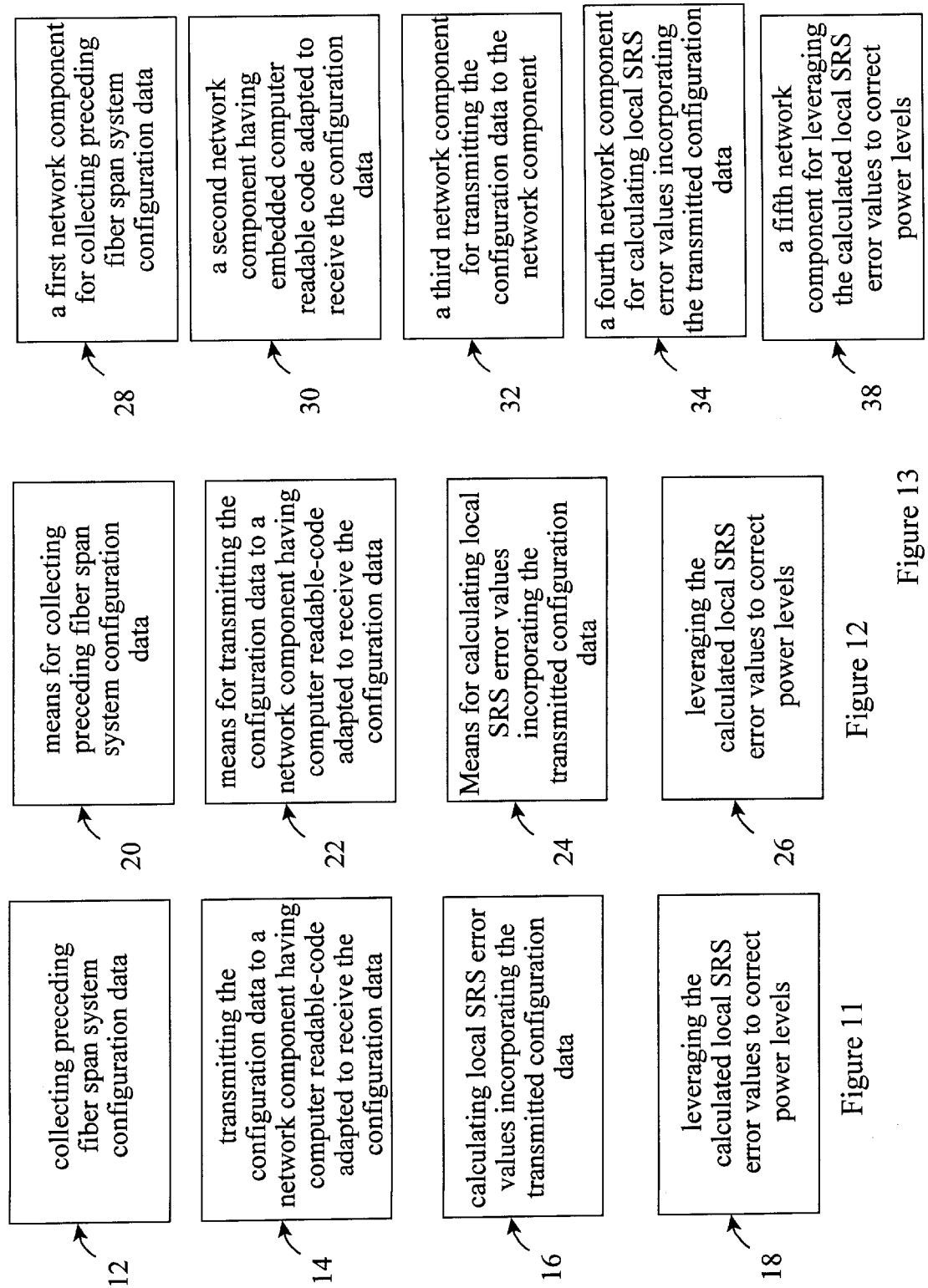

SYSTEM LEVEL STIMULATED RAMAN SCATTERING (SRS) COMPENSATION

FIELD OF THE INVENTION

The present invention relates to optical performance monitoring of an optical fiber network and more specifically to Stimulated Raman Scattering (SRS) error estimation and its effect on estimating the average power for each optical wavelength using the pilot tone method.

BACKGROUND OF THE INVENTION

Today's optical fiber networks carry many channels along their optical fibers. A significant challenge in maintaining these networks is the problem of power level estimation within these channels at every point in the network or in other words optical performance monitoring. A simple tool for optical performance monitoring and channel identification in DWDM (Dense Wave Division Multiplexing) systems is to add small signal sinusoidal dithers (pilot tones) to optical carriers. Consequently, each optical carrier has a unique sinusoidal dither whose amplitude is proportional to the average power of its carrier. These pilot tones are superimposed to the average power of the optical channel and can be separated and analysed easily. The presence of a specific dither at a particular point in the network therefore indicates the presence of its corresponding wavelength and its amplitude will show the average optical power.

This is true when each dither travels solely with its optical carrier. However, an effect known as Stimulated Raman Scattering (SRS) precipitates an inter-channel energy transfer that interferes with the ability to accurately estimate power levels through pilot tones. This inter-channel energy transfer occurs from smaller wavelengths to larger wavelengths causing larger wavelength power levels to increase. SRS not only causes an interaction between the average power of each channel but also brings about a transfer of dithers between different channels. Therefore, some of the dither of each channel is transferred to other channels and hence its amplitude will not be proportional to the power of its carrier any more. This causes inaccuracy in power level estimation using pilot tones. What is needed is a method of calculating the amount of SRS error at every point in the network and therefore provide a means to correct for the inaccuracy in power readings estimated by the pilot tone technique.

One way to correct for the inaccuracy resulting from the SRS on power estimation is to calculate the amount of SRS error in each span of the network prior to the node of interest and then adding all the calculated SRS errors to obtain the total error at that specific point. In other words, to compensate for SRS error by using local information for a given span. This approach is called "card level" compensation because it only needs the span number to estimate the error assuming that the global information of the network (number of wavelengths, fiber type, first span launch power) is already provided. In card level compensation identical characteristics for each span is assumed. Then the evolution of SRS error in one span is calculated. Finally, the total SRS error at a given point is estimated by adding each individual SRS error up to that point.

Although card level compensation provides a simple and reliable error estimation, it is typically inaccurate in the presence of severe SRS error. In order to accurately compensate for SRS error, the characteristics of the system at every span should be incorporated within the compensation process rather than the global information.

For the foregoing reasons, a need exists for a method of SRS error compensation in an optical fiber network that incorporates system configuration characteristics, or "system level compensation".

SUMMARY OF THE INVENTION

The present invention is directed to a method and apparatus for system level Stimulated Raman Scattering (SRS) error compensation for pilot tone measurements in an optical fiber network, the network characterized in that it comprises the infrastructure required to measure the power levels of all optical channels using a pilot tone monitoring technique, the compensation method comprising the steps of collecting preceding fiber spans system configuration data, transmitting the configuration data to a network component having computer readable-code adapted to receive the configuration data, calculating local SRS error values incorporating the transmitted configuration data and leveraging the calculated local SRS error values to correct power levels.

System level compensation provides for improved compensation for SRS error by providing to the compensation process important configuration information that has previously been unavailable. The inaccuracy in power readings due to SRS error can now be corrected at each amplifier with great accuracy.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

These and other features, aspects, and advantages of the present invention will become better understood with regard to the following description, appended claims, and accompanying drawings where:

FIG. 11 is an overview of a method for system level Stimulated Raman Scattering (SRS) error compensation in an optical fiber network according to the present invention;

FIG. 12 is an overview of an apparatus for system level Stimulated Raman Scattering (SRS) error compensation in an optical fiber network according to the present invention; and FIG. 13 is an overview of an apparatus for system level Stimulated Raman Scattering (SRS) error compensation in an optical fiber network according to the present invention.

DETAILED DESCRIPTION OF THE PRESENTLY PREFERRED EMBODIMENT

An embodiment of the method for system level Stimulated Raman Scattering (SRS) error compensation in an optical fiber network, the network characterized in that it comprises the infrastructure required to measure the power levels of all optical channels using a pilot tone monitoring technique, the compensation method comprises the steps of collecting preceding fiber spans system configuration data 12, transmitting the configuration data to a network component having computer readable-code adapted to receive the configuration data 14, calculating local SRS error values incorporating the transmitted configuration data 16 and leveraging the calculated local SRS error values to correct power levels 18.

The configuration data typically comprises, but is not limited to, the launch power of all wavelengths into the fiber, fiber type (optical properties), insertion loss, wavelength distribution and the local SRS error up to that point.

The local SRS error values are calculated using an SRS analytic equation substantially equal to $$P_s(z) = P_{s0} e^{-\alpha L} \left[ \left(1 + \frac{P_{p0} g}{\alpha}\right) + \frac{P_{p0} g}{\alpha} m\cos(\omega t) \right]$$

where $\alpha$ is the fiber attenuation and g is the Raman gain coefficient between channel $P_p$ and channel $P_s$.

This analytic equation is the solution of the non-linear system of differential equations describing the SRS phenomenon as discussed in Christodulides D. N and Jander R. B., "Evolution of Stimulated Raman Crosstalk in Wavelength Division Multiplexed Systems", IEEE Photonics Technology Letter, Vol. 8, No. 12, Dec. pp. 1722–1724, 1996, which is incorporated herein by this reference.

In order to accurately estimate SRS error, the information of the system configuration should be used at each amplifier. In other words, compensation should be performed at a "system level". Compared to card level compensation in which a general configuration for every span is assumed, in system level compensation the specific information of each span and the exact power distribution of every wavelength is provided to the model. For this purpose, the compensation algorithm at every span has access to the information of its previous span. Furthermore, in order to calculate the exact estimation of the SRS error the compensation algorithm takes the effect of the amplifiers gain profile into account. Finally, the compensation algorithm uses the SRS analytic equation to calculate the SRS error at every span.

Figure 1:
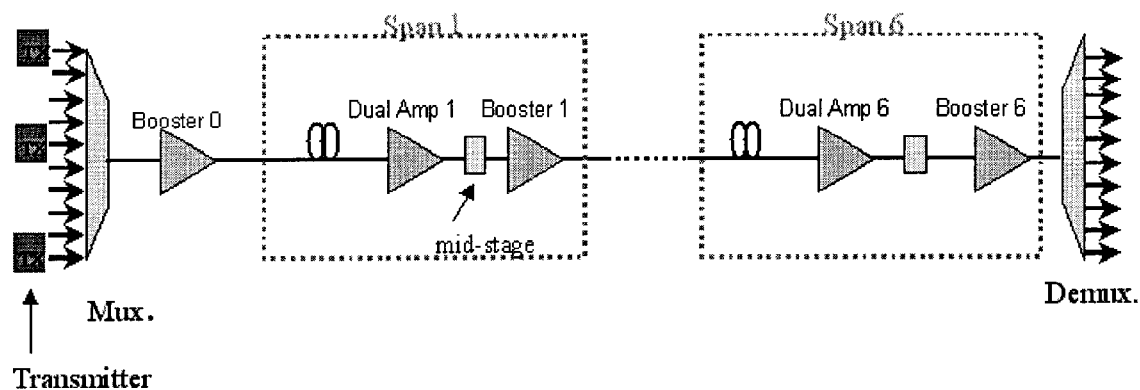
FIG. 1 shows a typical 6-span optical network with one dual and one booster amplifier in each span.

For SRS error calculation we consider a typical system comprised of a span fiber, a dual amplifier (pre-amplifier), a mid-stage module and a booster amplifier (power amplifier) as shown in FIG. 1. Starting from the first span, to calculate the SRS error the launch power per wavelength of the upstream booster is transmitted to the current dual amplifier. By having the information of the current span such as, but not necessarily limited to, fiber type, fiber length, insertion loss and wavelength distribution, the dual amplifier calculates the SRS error using the analytic equation. For this purpose the dual amplifier uses the output power of the upstream booster amplifier and the information of the current span in the analytic equation to calculate the distribution of the power at its input. This calculation is then repeated with the assumption that there is no SRS in the fiber. The difference of the power distributions of these two cases gives the error at the input of the dual amplifier.

In order to obtain the error profile at the output of the amplifier, the gain profile of the dual amplifier should be taken into account. The pilot tone technique provides both the input and the output powers of the amplifier per wavelength. Therefore, the gain profile can be easily calculated. Consequently, the SRS error profile with respect to the output power can be calculated. This power passes through the mid-stage module and then enters the booster amplifier. The same procedure is applied to the booster amplifier by transmitting the dual output power profile and the SRS error. Since, the mid-stage module normally includes a long fiber, such as 10–15 km, increasing SRS error, the system level compensation algorithm calculates error based on dual output power and the system configuration. Therefore, the SRS error at the input of the booster will include both span fiber and the mid-stage fiber errors. Once the SRS error profile at the input of the booster is calculated, the booster output error profile can be obtained. This error profile can now be used to compensate for the errors in power readings provided by pilot tone technique. The SRS error at the output of the booster and its output power per wavelength, which is the launch power into the next fiber span, is then sent to the next dual amplifier, where the procedure is repeated. The SRS error at every span includes the SRS error of its previous spans and the SRS error of its own span.

Figure 2:
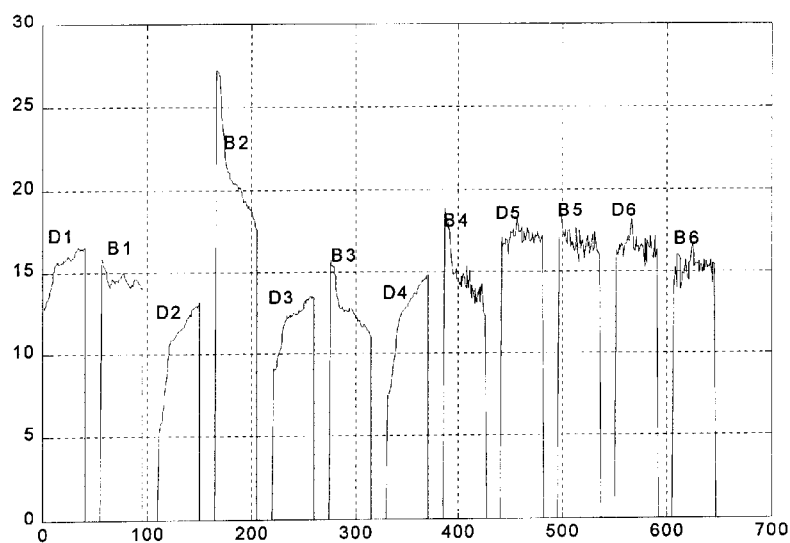
FIG. 2 shows the gain profile of each individual dual and booster in the NDSF 40 channel system with 6 dBm nominal launch power.
Figure 3:
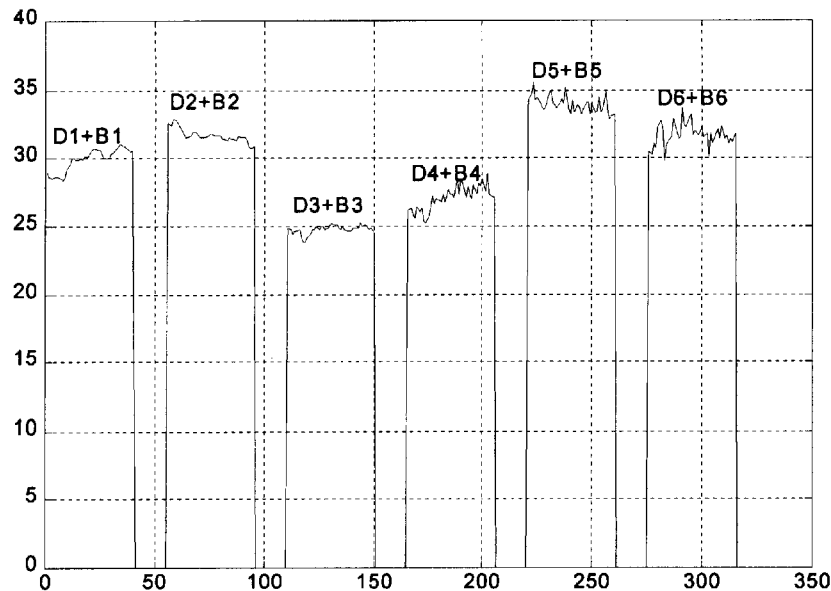
FIG. 3 shows despite the diversity in gain characteristic of each individual dual and booster the combination has an almost flat gain.

FIG. 2 shows the gain profile of each individual dual and booster in the NDSF 40-channel system with 6 dBm nominal launch power. Despite the diversity in gain characteristic of each individual dual and booster, the combination has an almost flat gain as shown in FIG. 3.

Figure 4:
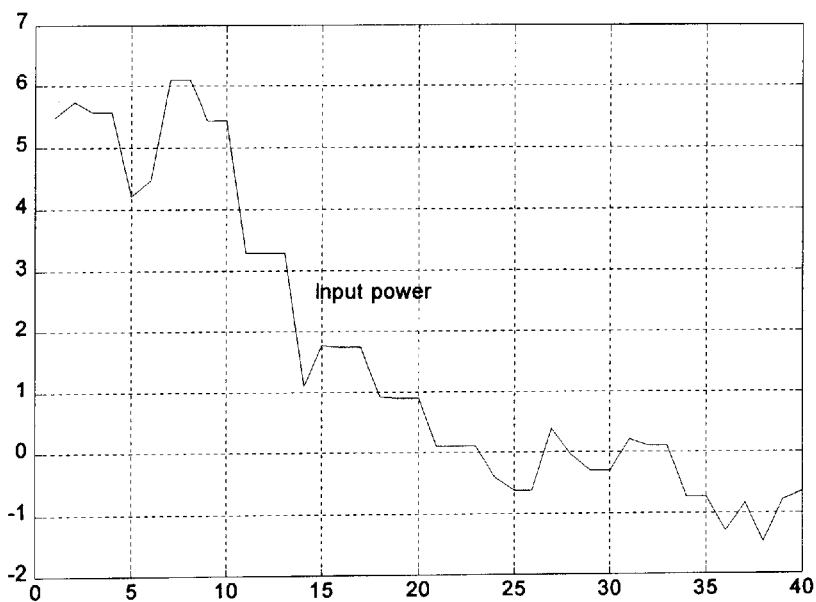
FIG. 4 shows the profile of the launch power per wavelength.
Figure 5:
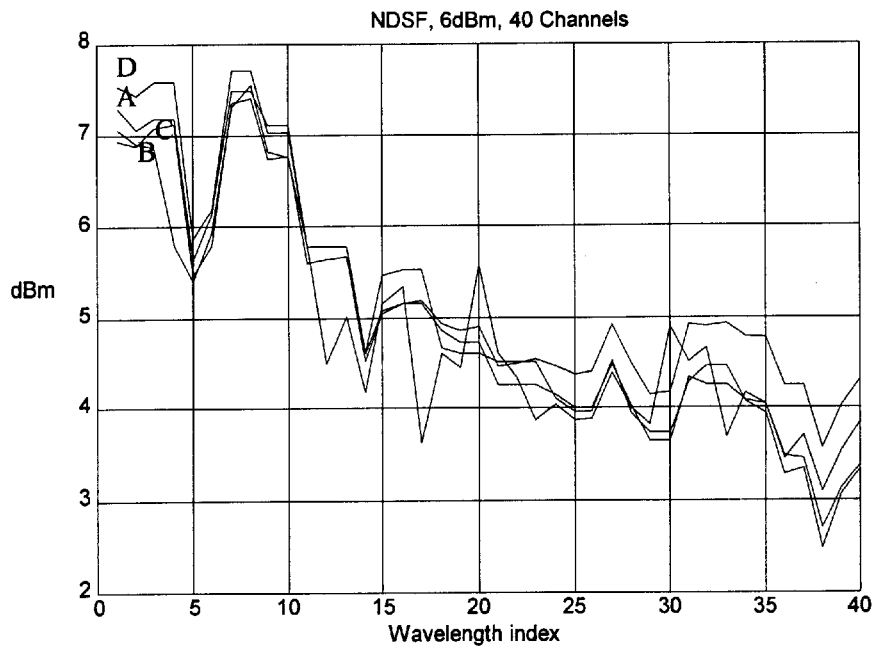
FIG. 5 shows actual and estimated powers at the first span.
Figure 6:
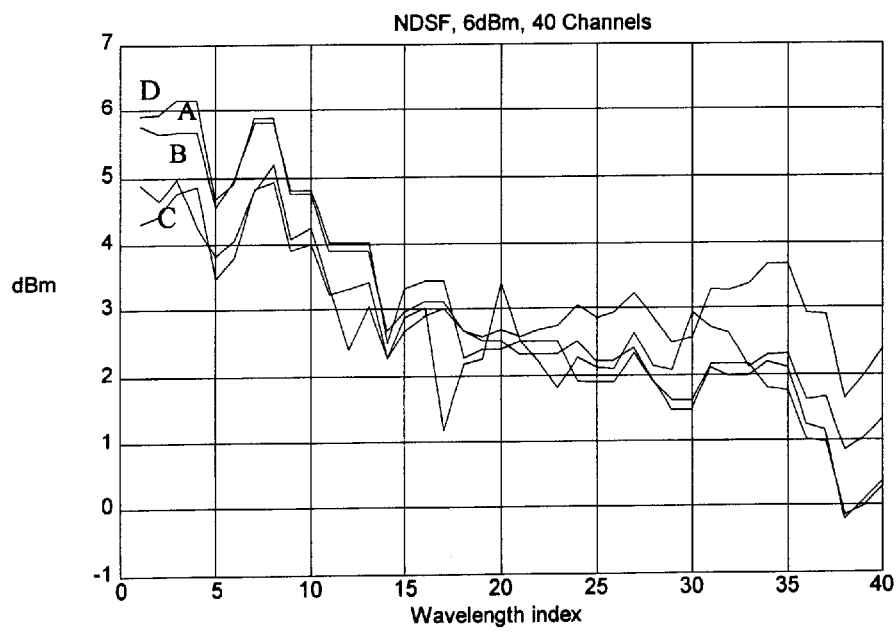
FIG. 6 shows actual and estimated powers at the second span.
Figure 7:
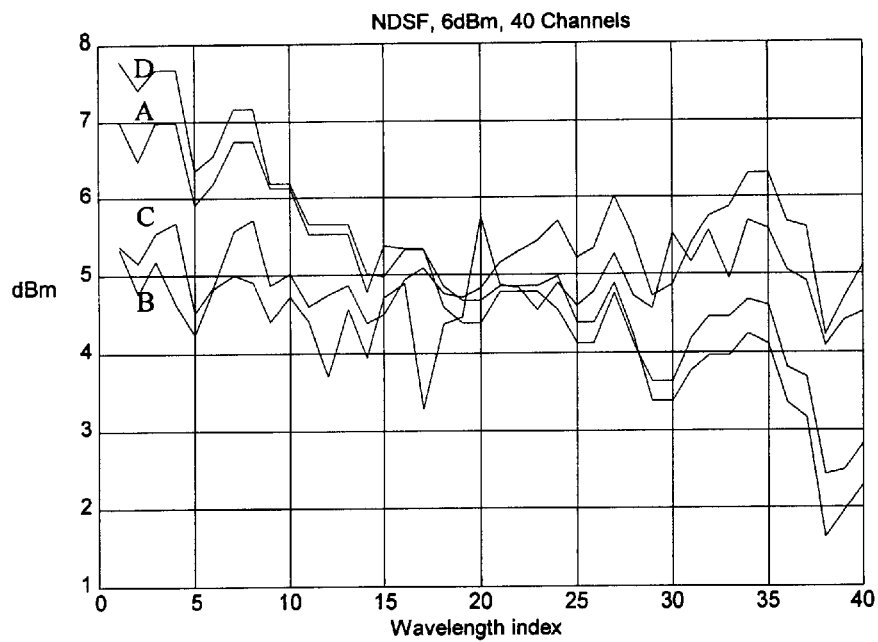
FIG. 7 shows actual and estimated powers at the third span.
Figure 8:
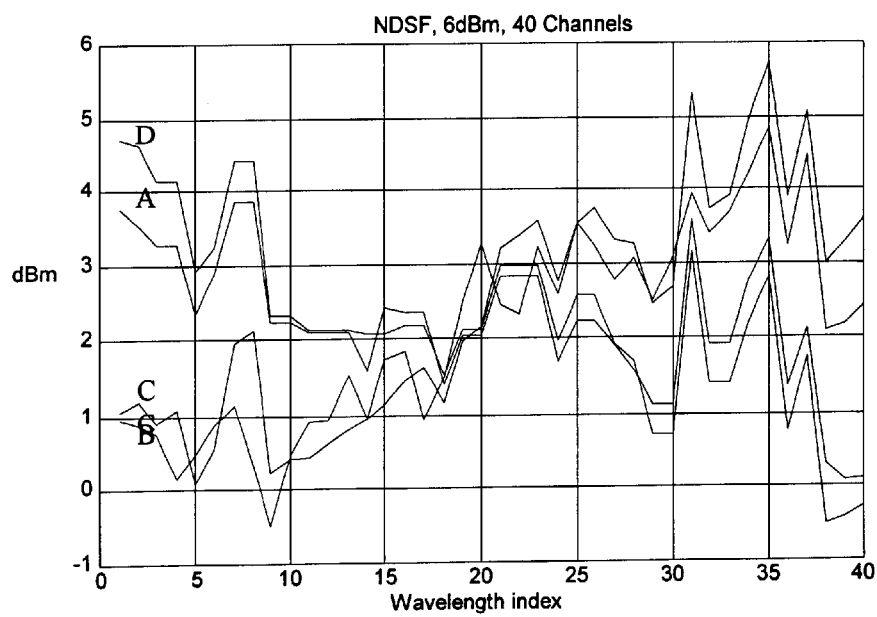
FIG. 8 shows actual and estimated powers at the fourth span.
Figure 9:
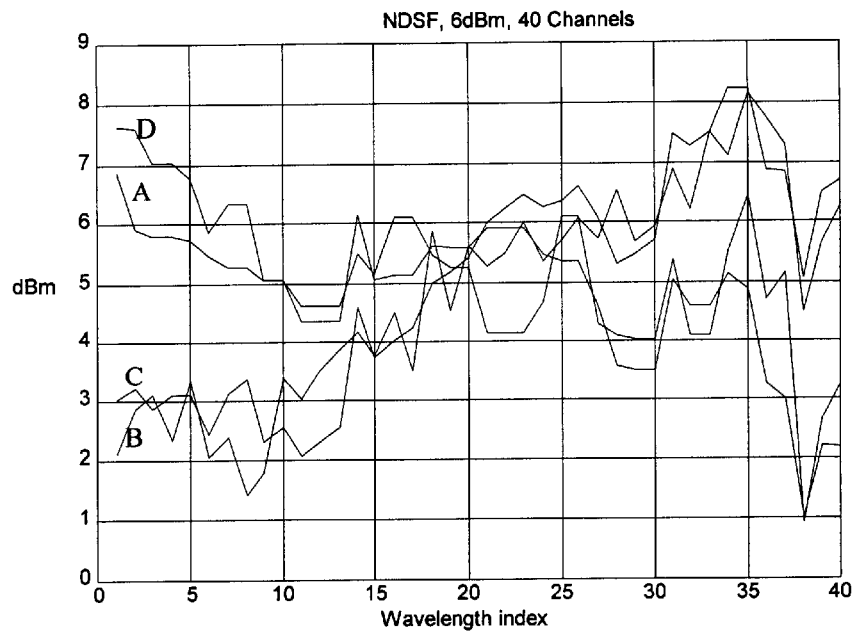
FIG. 9 shows actual and estimated powers at the fifth span.
Figure 10:
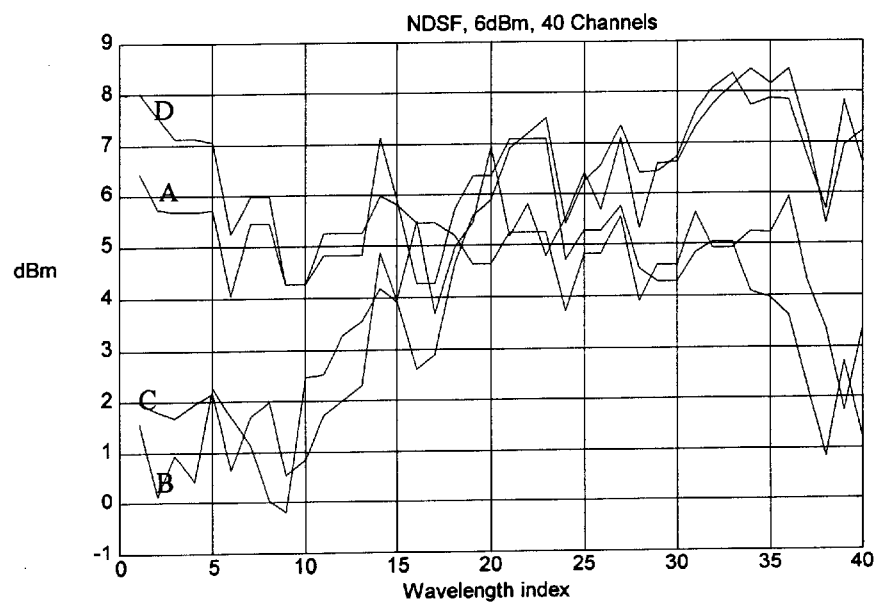
FIG. 10 shows actual and estimated powers at the sixth span.

The profile of the launch power per wavelength at the beginning of the system is shown in FIG. 4. If this power is injected into the system, then the distribution of power at each point within the system, and thus the SRS impact, can be calculated.

FIGS. 5 through 10 display the results of applying the SRS analytic equation to estimate the SRS error at every span for a 6-span, 40-channel NDSF system. In these figures we have:

A: Pilot tone power measurement (Experimental)

B: Optical spectral analyzer (OSA) measurement (Experimental)

C: Optical spectral analyzer (OSA) measurement (Model)

D: Pilot tone power measurement (Model)

In every span we have experimentally measured the actual power provided by an optical spectral analyzer (OSA) and the pilot tone supervisory technique. The same quantities produced by the system level compensation algorithm are also shown in these figures. The compensation algorithm provides accurate results despite severe SRS error at the last spans.

System under study:

NDSF 40 channel, 6 dBm nominal power per wavelength. Mid-stage access includes a dispersion compensated fiber (DCM) 15 km, span fiber length 80 km with a combination of dual and booster 21 amplifiers at every span.

Attenuation for span fiber=0.2 dB/km

Attenuation for DCM fiber=0.5 dB/km

FIGS. 5 through 10 illustrate actual and estimated powers at different spans. The power measured by OSA is in fact the actual average optical power while the pilot tone power includes the average optical power plus the SRS error. Recalling that the OSA is not available in practice in the system. Pilot tone power levels are those which are available for power level estimation and should be corrected for the SRS error.

As shown in FIGS. 5 through 10, the experimental power levels are compared with the estimated power levels generated by the system level compensation algorithm. It can be seen that the estimated powers closely follow the actual powers. In other words, the system level compensation enables estimation of actual power (OSA model) and to compensate for SRS error, (the difference between the OSA model and pilot tone model), with high accuracy.

Although the present invention has been described in considerable detail with reference to certain preferred versions thereof, other versions are possible. Therefore, the spirit and scope of the appended claims should not be limited to the description of the preferred versions contained herein.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. A method for system level Stimulated Raman Scattering (SRS) error compensation in an optical fiber network, the network characterized in that it comprises the infrastructure required to measure the power levels of all optical channels using a pilot tone monitoring technique, the compensation method comprising the steps of:

(i) collecting preceding fiber span system configuration data;
   (ii) transmitting the configuration data to a network component having computer readable-code adapted to receive the configuration data;
   (iii) calculating local SRS error values incorporating the transmitted configuration data; and
   (iv) leveraging the calculated local SRS error values to correct power levels.

2. An apparatus for system level Stimulated Raman Scattering (SRS) error compensation in an optical fiber network, the network characterized in that it comprises the infrastructure required to measure the power levels of all optical channels using a pilot tone monitoring technique, the compensation apparatus comprising:

means for collecting preceding fiber span system configuration data;
   a network component having embedded computer readable code adapted to receive the configuration data;
   means for transmitting the configuration data to the network component;
   means for calculating local SRS error values incorporating the transmitted configuration data; and
   means for leveraging the calculated local SRS error values to correct power levels.

3. An apparatus for system level Stimulated Raman Scattering (SRS) error compensation in an optical fiber network, the network characterized in that it comprises the infrastructure required to measure the power levels of all optical channels using a pilot tone monitoring technique, the compensation apparatus comprising:

a first network component for collecting preceding fiber span system configuration data;
   a second network component having embedded computer readable code adapted to receive the configuration data;
   a third network component for transmitting the configuration data to the network component;
   a fourth network component for calculating local SRS error values incorporating the transmitted configuration data; and
   a fifth network component for leveraging the calculated local SRS error values to correct power levels.

* * * * *

UNITED STATES PATENT AND TRADEMARK OFFICE
CERTIFICATE OF CORRECTION

PATENT NO. : 6,519,066 B2  
APPLICATION NO. : 09/887445  
DATED : February 11, 2003  
INVENTOR(S) : Seydnejad et al.

It is certified that error appears in the above-identified patent and that said Letters Patent is hereby corrected as shown below:

On Title Page  
Item (73) is omitted and should read: Assignee, NORTEL NETWORKS LIMITED, Montreal (CA)

Signed and Sealed this

Eighteenth Day of July, 2006

JON W. DUDAS  
*Director of the United States Patent and Trademark Office*